United States Patent [19]

Sellstedt et al.

[11] 4,076,718

[45] Feb. 28, 1978

[54] 2,6-PYRIDINEDIYL-BIS-TETRAZOL-5-CARBOXAMIDES

[75] Inventors: John H. Sellstedt, Pottstown; Dieter H. Klaubert, West Chester, both of Pa.

[73] Assignee: American Home Products Corporation, New York, N.Y.

[21] Appl. No.: 761,150

[22] Filed: Jan. 21, 1977

[51] Int. Cl.$^2$ .................. C07D 401/14; A61K 31/455
[52] U.S. Cl. ...................... 260/295 PA; 260/295 AM; 260/308 D; 424/266
[58] Field of Search ............................... 260/295 AM

[56] References Cited

U.S. PATENT DOCUMENTS 3,622,596  11/1971  Fischer et al. ............... 260/295 AM

*Primary Examiner*—Natalie Trousof
*Assistant Examiner*—Cary Owens
*Attorney, Agent, or Firm*—Richard K. Jackson

[57] ABSTRACT

Anti-allergic agents of N,N'-(2,6-pyridinediyl)bis(1H-tetrazole-5-carboxamide derivation, pharmaceutically acceptable salts thereof and N-protected intermediates therefor.

5 Claims, No Drawings

2,6-PYRIDINEDIYL-BIS-TETRAZOL-5-CARBOXAMIDES

BACKGROUND OF THE INVENTION

Atopic immediate sensitivity is the chief manifestation found in animals suffering from bronchial asthma, seasonal pollinosis (e.g. hay fever), allergic rhinitis, urticaria, allergic conjunctivitis, food allergies and anaphylactoid reactions. The substances most frequently responsible for clinically manifest sensitivities are plant pollen, animal feathers and danders, dust, milk and wheat, whether inhaled or ingested. Atopic hypersensitivity is found in man, dog, and other animals. Its occurance is exceptionally found in the lower animals.

The presence of antibodies associated with atopic hypersensitivity reactions in the host serum is established by the passive sensitization of the skin of a normal recipient, after injection of serum from a sensitized host into a skin site followed by injection of antigen into the same area 24 hours later, resulting in a local hive. This is commonly referred to as the Prausnitz-Kustner (P-K) reaction.

The antibody associated with atopic hypersensitivity possesses distinctive features in that it does not in all forms precipitate with its antigen, fails to pass the placenta from mother to fetus, has special affinity for the skin, frequently lacks specificity toward an individual antigenic factor and is usually labile at about 56° C. after two hours.

The homocytotropic antibody found in or induced in the rat is related in function and reaction to immunoglobulin E (reagin or IgE) found in the human. The correlation between homocytotropic antibody in the rat and IgE in the human has been established through the common effects obtained from chemical reactions, immunological reactions and drug responses in the two species hosting those antibodies. In the human, reagin is the antibody responsible for atopic immediate hypersensitive reactions. In the rat, the homocytotropic antibody is responsible for atopic immediate hypersensitive reactions.

In theory, reagin, influences the cell membrane of a mast cell by reacting with an antigen, to initiate the reaction(s) within the mast cell which ultimately releases a mediator such as Bradykinin, SRS-A (slow reacting substance-A), histamine and other unknown substances. The mediator effects a change in surrounding cell wall permeability permitting a rapid change in flow or exudance of mediator(s) from the cells, resulting in an allergic attack symptom. The various methods commonly employed to relieve the symptoms of allergic attack, none of which are considered to be quite acceptable, are to (1) avoid attack by the antigen, (2) block the production of antibody with an immunosuppressant, (3) block the action of the mediators on the cell under attack by administration of anti-histaminics, anti-5-hydroxy-tryptamines(5-HT) or anti-inflammatories, or (4) stimulate the cell under attack to negate the action of the mediator through the action of bronchodilators such as Isuprel ® or a Xanthine.

A compound typifying anti-allergic activity by blocking reaction(s) within the mast cells, thereby preventing the production and release of mediators, is disodium cromoglycate. (INTAL ®).

DESCRIPTION OF THE INVENTION

In accordance with this invention there is provided a group of anti-allergic agents of the formula:

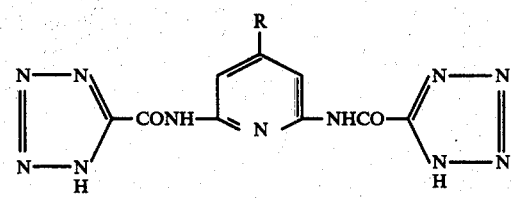

in which
R is hydrogen, halo or lower alkoxy, or a pharmaceutically acceptable salt thereof. In addition, this invention provides protected intermediates employed in the production of the 2,6-pyridinediyl-bis-tetrazole-5-carboxamides, which intermediates present the structural formula:

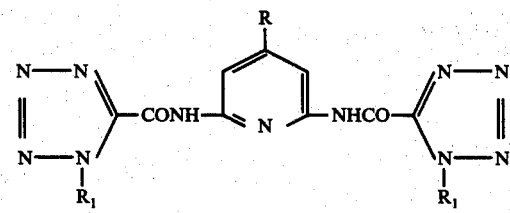

in which
R is defined supra, and the two $R_1$ groups represent any readily removable protective group such as those described by F. Weygand et al., Deut. Ber. Chem. 101, 3623–3641(1968). For example, the protective group may be benzyl, 4-methoxybenzyl, 2,4-dimethoxybenzyl, 2,4,6-trimethoxybenzyl, and the like.

The pharmaceutically acceptable salts of the 2,6-pyridinediyl-bis-tetrazole-5-carboxamides of this invention are the alkali metal (e.g. sodium or potassium), the alkaline earth metal (e.g. calcium or magnesium), lower alkyl amine (e.g. ethylamine, i-propylamine, n-propylamine, etc.), di-lower alkylamine(e.g. dimethylamine, diethylamine, etc.), tri-lower alkylamine (e.g. trimethylamine, triethylamine, tripropylamine, etc.) or a water solubilizing amine such as the omega hydroxy analogues of the primary and secondary lower alkylamines as well as more complex amines such as N,N'-dibenzylethylenediamine.

Throughout this disclosure, the term "lower" used to modify such terms as alkoxy, alkylamine, etc. is intended to define the carbon atom content of the modified term as from 1 to 6 carbon atoms per hydrocarbon radical. The term "halo" is intended to embrace the chloro, bromo and iodo groups. It should also be understood that the tetrazole moieties depicted as 1H-tetrazole-5-carboxamides may appear when unprotected as the 2H-tautomer and it is applicants intent to embrace the 2H-tautomer as the full equivalent of the depicted 1H-tautomer. The tautomers may be depicted as follows:

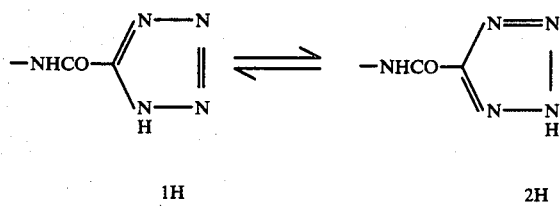

The compounds of this invention are prepared by reaction of an appropriately substituted 2,6-pyridinediyldiamine with two equivalents of 1-protected-1H-tetrazole-5-carbonyl chloride followed by deprotection of the tetrazole moieties and conversion to a desired pharmaceutically acceptable salt when water solubility is desired. Thus,

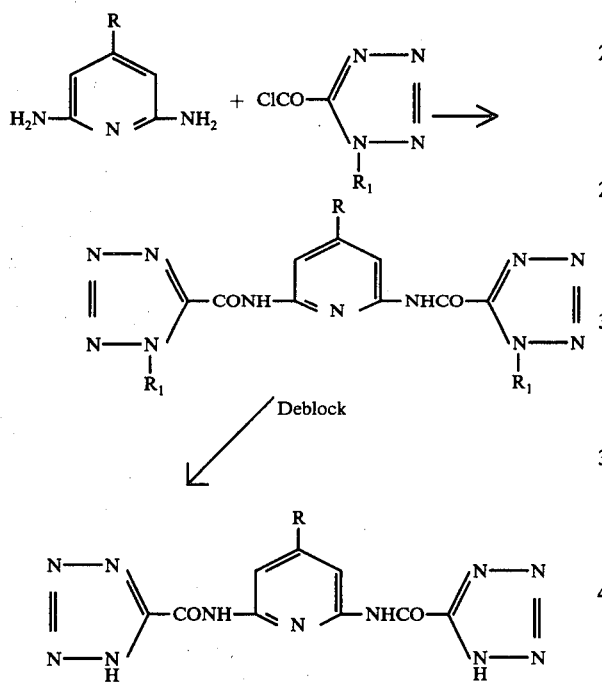

The 2,6-diaminopyridine reactants are known compounds or may be readily prepared by techniques well known to the chemist. The 1-protected-1H-tetrazole-5-carbonyl chloride reactant is prepared by the procedure disclosed in our copending application Ser. No. 669,570 filed March 23, 1976. Deprotection of the tetrazole moieties after condensation with the pyridine diamine is performed by methods well known in the art.

The anti-allergy compounds of this invention relieve atopic allergic manifestations when administered orally, topically, intraperitoneally, intramuscularly, intravenously and as inhalents.

The technique employed to establish the anti-allergic activity of the bis-1H-tetrazole-5-carboxamide derivatives of this invention is reported in Immunology, vol. 16, pp. 749–760 (1969) and involves four male Charles River rats (200–250 grams body weight) per group to provide a control, a host for administration of a standard anti-allergic compound (disodium cromoglycate) and animals for the test compound. The rats were injected intracutaneously on their shaved backs with sera from rats immunized with egg albumin and pertussis vaccine. Forty-eight hours after the initial injections, the test compound is administered at graded dosage levels by the desired route. Five minutes later one milliliter of a 0.8 percent solution of ovalbumin containing 5 mg. of Evans blue dye is injected intravenously. After forty minutes, the animal is sacrificed and the bleb size on its back is measured. The mean bleb size for the animals administered the test compound is calculated and the percent inhibition is determined by comparison with the control animal.

Although the mechanism by which the compounds of this invention function is not absolutely known, applicants have found that the compounds of this invention, in a manner believed to be similar to the function of INTAL ®, block reaction(s) in the mast cell leading to the production and release of mediators.

The compounds of this invention permit the occurrence of a non-productive antigen-antibody interaction. They effectively block the IgE type reaction and have little or no effect on the other immunoglobulins such as IgG, IgM, IgA and IgD.

In other words, the compounds of this invention block the release of mediators commonly resulting from the antigen-antibody reaction as exemplified in a passive cutaneous anaphylaxis test (PCA) using rat homocytotropic antibody — a known correlate of human reaginic antibody.

By analogy to disodium cromoglycate and its activity correlation between standard test animals, domestic animals and man, the compounds of this invention have been established as anti-allergic agents suitable for the same uses at analogous doses and through the same route of administration as INTAL ®.

Thus, there is provided herewith the means for suppressing allergic manifestations of atopic immediate sensitivity in warm-blooded, human and non-human animals, the latter including domesticated animals such as the mouse, rat, hamster, gerbil, dog, cat, sheep, goat, horse, cow, and the like, by administering an effective amount of one or more of the compounds disclosed in this application by oral, topical, intraperitoneal, intramuscular or intravenous routes as well as via inhalation. The compounds of this invention may be administered in conjunction with known compounds effecting antihistaminic, anti-hypertensive, analgesic, central nervous system depressant, immunosuppressive, anti-serotonin, anti-Bradykinin or endocrinological responses. In addition, those conventional adjuvants known to the art may be combined with the anti-allergics of this invention to provide compositions and solutions for administrative purposes, although it is considered desirable and feasible to employ the anti-allergies as neat or pure compounds without additives other than for purposes of providing suitable pharmaceutical solution or liquid or vapor suspensions, the latter for use as inhalants. Aqueous solutions are readily formed with the metal salts of this invention.

The following specifically exemplified compounds demonstrated at least 68 percent inhibition of the mean bleb size at a dosage of 1 milligram per kilogram host body weight to 100 percent inhibition at 1 mg/kg when administered intraperitoneally, the product of Example 1 demonstrating 40 percent inhibition at a dose as low as 0.01 mg/kg. The percent inhibition evidenced by the product of Example 2 upon oral administration is illustrative of the other compounds of this invention, increasing from 32 percent inhibition at 0.1 mg/kg to 65 percent at 1.0 mg/kg to 77 percent at 10 mg/kg to 70 percent at 50 mg/kg and 97 percent at 100 mg/kg. Thus the effective dose varies with the route of administration, lying within the range of between 0.01 to 100.0 milligrams per kilogram host body weight. Hence, for practical administration the unit dosage contemplated for human and non-human use based upon the potency of the compound administered lie from about 1.0 milligram to about 1 gram to be administered when necessary and the the degree of the desired response, in single or plural doses under the guidance of a physician.

EXAMPLE 1

N,N'-(2,6-Pyridinediyl)bis[1H-tetrazole-5-carboxamide]Disodium Salt 1-(4-Methoxybenzyl)-1H-tetrazole-5-carbonyl chloride (17.7 g., 0.07 mol.) in 400 ml. of cold methylene chloride is dripped into a solution of 3.82 g. (0.035 mol.) of 2,6-diaminopyridine and 5.83 ml. (0.072 mol.) of pyridine in 200 ml. of tetrahydrofuran at 0°–5° C. over 10 min. The solution is stirred for 2 hours at room temperature and then kept at room temperature overnight. Water is added, the layers are separated, and the aqueous layer is extracted with methylene chloride. The organic layer is washed two times with water once with brine, and is dried with sodium sulfate. Evaporation and crystallization of the residue from acetonitrile gives 14.1 g. of N,N'-(2,6-pyridinediyl)bis[1-(4-methoxyphenylmethyl)-1H-tetrazole-5-carboxamide], m.p. 188°–91° C.

Anal. Calcd. for $C_{25}H_{33}N_{11}O_4$: C, 55.45; H, 4.28; N, 28.45. Found: C, 56.67; H, 4.26; N, 29.39.

The protected tetrazole (13.34 g., 0.0246 mol.) and 26.9 ml. (0.249 mol) of anisole are refluxed in 319 ml. of trifluoroacetic acid for 30 minutes under nitrogen, and the mixture is then cooled in an ice bath. The solvent is removed on a rotary evaporator at 40° C., and the residue is triturated with diethyl ether. The mixture is filtered and the cake is washed with diethyl ether giving 4.46 g. of N,N'-(2,6-pyridinediyl)-bis(1H-tetrazole-5-carboxamide) as a white solid.

The tetrazole (4.35 g., 0.0125 mol.) is dissolved in 10 ml. of water by the addition of 25 ml. of 1.000N sodium hydroxide. The solution is filtered, and the filtrate is freeze-dried giving 4.5 g. of the title compound as a white salt, m.p. > 300° C.

Anal. Calcd. for $C_9H_5N_{11}Na_2O_2 \cdot 2.98H_2O$: C, 27.09; H, 2.77; N, 38.61. Found: C, 27.09; H, 2.02; N, 38.12.

EXAMPLE 2

N,N'-(4-Chloro-2,6-pyridinediyl)bis[1H-tetrazole-5-carboxamide]Disodium Salt

In a manner similar to example 1, but starting with 2,6-diamino-4-chloropyridine (5.05 g., 0.035 mol.), the intermediate N,N'-(4-chloro-2,6-pyridinediyl)bis[1-(4-methoxyphenylmethyl)-1H-tetrazole-5-carboxamide] is prepared (10.17 g., m.p. 201°–203° C. from ethyl acetate).

Anal. Calcd. for $C_{25}H_{22}ClN_{11}O_4$: C, 52.13; H, 3.85; N, 26.75; Cl, 6.16. Found: C, 51.87; H, 3.84; N, 26.71; Cl, 6.55.

In a manner similar to example 1, 10 g. of the above protected tetrazole is deprotected, the sodium salt (2.59 g.) is produced and collected as crystals from water, m.p. > 300° C.

Anal. Calcd. for $C_9H_4ClN_{11}Na_2O_2 \cdot 0.42H_2O$: C, 27.92; H, 1.26; N, 39.80. Found: C, 27.92; H, 1.19; N, 39.74.

EXAMPLE 3

N,N'-(4-ethoxy-2,6-pyridinediyl)bis[1H-tetrazole-5-carboxamide]Disodium salt

Following the procedure of example 1 with the exception that 2,6-diamino-4-ethoxypyridine is substituted for 2,6-diaminopyridine, there is obtained the title compound.

The product of Examples 1 and 2 exhibit anti-secretory activity when tested in the four hour pylorus ligated rat test according to the procedure of Shay et al., Gastroenterology 26 906–913 (1954) at from about 0.1 to 10 milligrams per kilogram host body weight and at 100 milligrams per kilogram host body weight, respectively.

What is claimed is:

1. A compound of the formula:

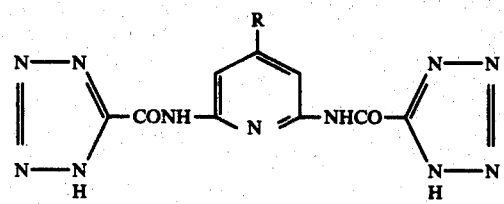

in which

R is hydrogen, halo or lower alkoxy, or a pharmaceutically acceptable salt thereof.

2. A compound of claim 1 which is N,N'-(2,6-pyridinediyl)bis(1H-tetrazole-5-carboxamide) or a pharmaceutically acceptable salt thereof.

3. A compound of claim 1 which is N,N'-(4-chloro-2,6-pyridinediyl)bis(1H-tetrazole-5-carboxamide) or a pharmaceutically acceptable salt thereof.

4. A compound of claim 1 which is N,N'(4-ethoxy-2,6-pyridinediyl)bis(1H-tetrazole-5-carboxamide) or a pharmaceutically acceptable acid addition salt thereof.

5. A compound of the formula:

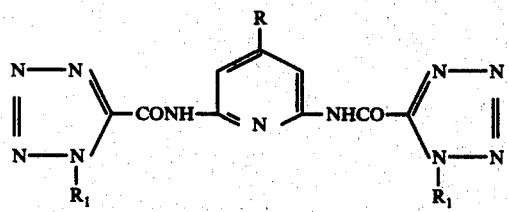

in which

R is hydrogen, halo or lower alkoxy; and $R_1$ is benzyl, 4-methoxybenzyl, 2,4-dimethoxybenzyl; or 2,4,6-trimethoxybenzyl.

* * * * *